(12) United States Patent  
Ravikumar et al.

(10) Patent No.: US 10,856,901 B2  
(45) Date of Patent: Dec. 8, 2020

(54) EXCHANGER SURGICAL ACCESS PORT ASSEMBLY AND METHODS OF USE

(71) Applicant: TELEFLEX MEDICAL INCORPORATED, Morrisville, NC (US)

(72) Inventors: Sundaram Ravikumar, Briarcliff Manor, NY (US); Guy Osborne, Trumbull, CT (US); Harry Allan Alward, Shelton, CT (US)

(73) Assignee: Teleflex Medical Incorporated, Morrisville, NC (US)

( * ) Notice: Subject to any disclaimer, the term of this patent is extended or adjusted under 35 U.S.C. 154(b) by 883 days.

(21) Appl. No.: 15/022,910

(22) PCT Filed: Sep. 19, 2014

(86) PCT No.: PCT/US2014/056456  
§ 371 (c)(1),  
(2) Date: Mar. 17, 2016

(87) PCT Pub. No.: WO2015/047886  
PCT Pub. Date: Apr. 2, 2015

(65) Prior Publication Data  
US 2016/0228148 A1    Aug. 11, 2016

Related U.S. Application Data

(60) Provisional application No. 61/879,468, filed on Sep. 18, 2013, provisional application No. 62/024,999, filed on Jul. 15, 2014.

(51) Int. Cl.  
*A61B 1/32* (2006.01)  
*A61B 17/34* (2006.01)  
*A61B 17/29* (2006.01)  
*A61B 17/00* (2006.01)

(52) U.S. Cl.  
CPC .......... *A61B 17/3421* (2013.01); *A61B 17/29* (2013.01); *A61B 2017/0042* (2013.01); *A61B 2017/2901* (2013.01)

(58) Field of Classification Search  
CPC combination set(s) only.  
See application file for complete search history.

(56) References Cited

U.S. PATENT DOCUMENTS

| | | |
|---|---|---|
| 5,282,800 A | 2/1994 | Foshee et al. |
| 5,413,561 A | 5/1995 | Fischell et al. |
| 5,454,790 A | 10/1995 | Dubrul |
| 5,456,673 A | 10/1995 | Ziegler et al. |
| 5,505,710 A * | 4/1996 | Dorsey, III ........... A61M 1/008 604/158 |
| 5,626,597 A | 5/1997 | Urban et al. |

(Continued)

FOREIGN PATENT DOCUMENTS

| | | |
|---|---|---|
| CN | 1695566 A | 11/2005 |
| CN | 101586725 A | 11/2009 |

(Continued)

*Primary Examiner* — Sameh R Boles  
(74) *Attorney, Agent, or Firm* — BakerHostetler

(57) ABSTRACT

A surgical access port assembly including a cannula having a diameter of less than about 3 mm and a tapered hub, capable of attachment to a laparoscopic surgical instrument, connected to the proximal end of the cannula.

17 Claims, 9 Drawing Sheets

(56) References Cited

U.S. PATENT DOCUMENTS

| | | | |
|---|---|---|---|
| 5,759,188 A | 6/1998 | Yoon | |
| 5,868,714 A | 2/1999 | Danks | |
| 6,159,224 A | 12/2000 | Yoon | |
| 6,197,002 B1 | 3/2001 | Peterson | |
| 6,224,569 B1 * | 5/2001 | Brimhall | A61M 25/0618 |
| | | | 604/164.06 |
| 6,336,914 B1 | 1/2002 | Gillespie, III | |
| 7,766,937 B2 | 8/2010 | Ravikumar | |
| 8,133,255 B2 | 3/2012 | Ravikumar | |
| 8,230,863 B2 | 7/2012 | Ravikumar et al. | |
| 8,313,507 B2 | 11/2012 | Ravikumar | |
| 8,956,351 B2 | 2/2015 | Ravikumar et al. | |
| 9,326,784 B2 | 5/2016 | Ravikumar | |
| 9,486,238 B2 | 11/2016 | Ravikumar et al. | |
| 9,492,187 B2 | 11/2016 | Ravikumar et al. | |
| 10,166,038 B2 | 1/2019 | Ravikumar et al. | |
| 10,368,907 B2 | 8/2019 | Ravikumar et al. | |
| 10,390,852 B2 | 8/2019 | Ravikumar et al. | |
| 10,537,347 B2 | 1/2020 | Ravikumar et al. | |
| 2003/0130693 A1 | 7/2003 | Levin et al. | |
| 2006/0074374 A1 | 4/2006 | Gresham | |
| 2007/0088277 A1 | 4/2007 | McGinley et al. | |
| 2007/0093755 A1 | 4/2007 | Koos et al. | |
| 2007/0093790 A1 | 4/2007 | Downey et al. | |
| 2007/0250112 A1 | 10/2007 | Ravikumar et al. | |
| 2007/0282170 A1 | 12/2007 | Ravikumar | |
| 2008/0215078 A1 | 9/2008 | Bennett | |
| 2010/0016884 A1 | 1/2010 | Ravikumar | |
| 2010/0222747 A1 | 9/2010 | Wenchell et al. | |
| 2010/0292724 A1 | 11/2010 | Ravikumar et al. | |
| 2011/0046449 A1 | 2/2011 | Minnelli et al. | |
| 2011/0160538 A1 | 6/2011 | Ravikumar et al. | |
| 2012/0080483 A1 | 4/2012 | Riestenberg et al. | |
| 2012/0277576 A1 | 11/2012 | Lui | |
| 2017/0156789 A1 | 6/2017 | Ravikumar et al. | |
| 2017/0224413 A1 | 8/2017 | Ravikumar et al. | |

FOREIGN PATENT DOCUMENTS

| | | |
|---|---|---|
| CN | 102510739 A | 6/2012 |
| EP | 0 647 429 A2 | 4/1995 |
| EP | 1516592 B1 | 3/2007 |
| JP | S58-133348 U | 9/1983 |
| JP | H02-15159 U | 1/1990 |
| JP | H09-512732 A | 12/1997 |
| JP | 2003510137 A | 3/2003 |
| JP | 2008-253585 A | 10/2008 |
| JP | 2009-529983 A | 8/2009 |
| JP | 2010-207260 A | 9/2010 |
| JP | 2011-212458 A | 10/2011 |
| JP | 2012-165958 A | 9/2012 |
| JP | 2013-106771 A | 6/2013 |
| JP | 2013-248222 A | 12/2013 |
| WO | 2007/050969 A2 | 5/2007 |
| WO | 2012/044815 A1 | 4/2012 |

* cited by examiner

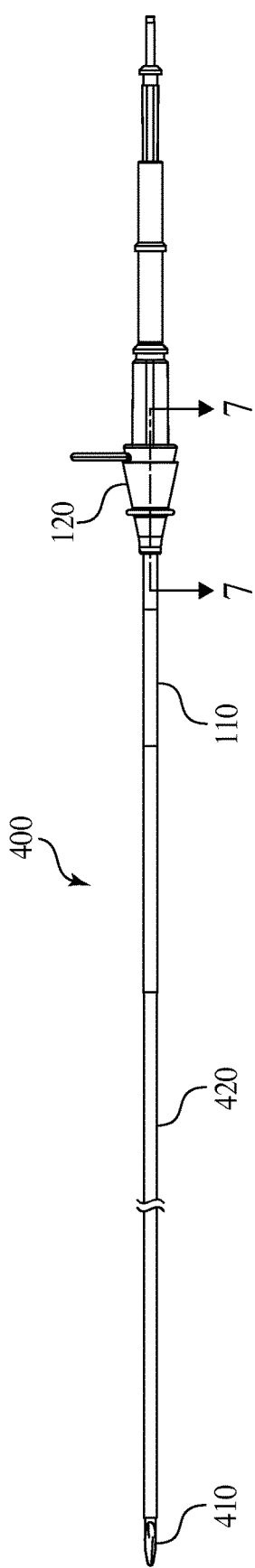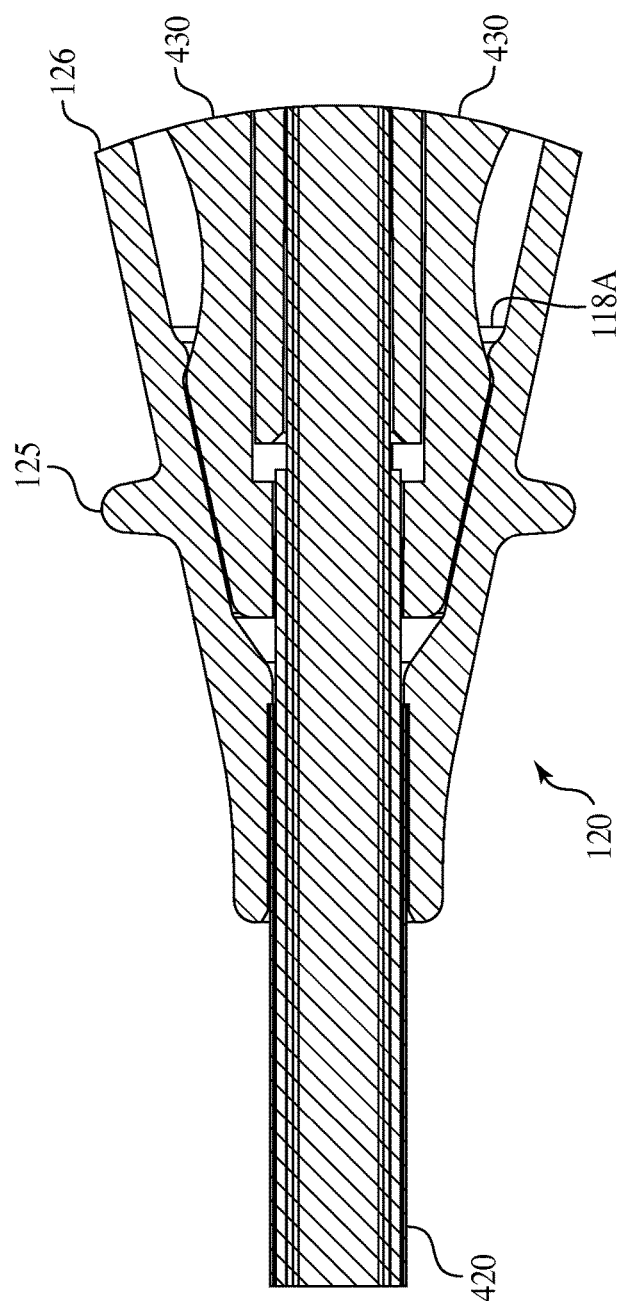

EXCHANGER SURGICAL ACCESS PORT ASSEMBLY AND METHODS OF USE

RELATED APPLICATIONS

This application claims priority from a provisional application filed on Sep. 19, 2013, No. 61/879,468 and another filed Jul. 15, 2014, No. 62/024,999.

BACKGROUND OF THE INVENTION

Field of the Invention

The present invention relates to surgical instruments and methods of their use, and more particularly to minimally invasive surgical instruments, an exchanger surgical access port assembly and methods using an exchanger surgical access port so that multiple surgical instruments can be used therein.

Description of Related Art

Over the last two decades, minimally invasive surgery has become the standard for many types of surgeries which were previously accomplished through open surgery. Minimally invasive surgery generally involves introducing an optical element (e.g., laparoscopic or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly.

The trocar assembly often includes a port, a pointed element extending through and beyond the distal end of the port, and at least in the case of abdominal laparoscopy, a sealing valve on the proximal portion of the port. The term trocar typically includes a combination of cooperating elements such as a cannula, a seal housing and an obturator. First the obturator, which has a blunt or pointed edge, cuts or pierces the body wall so that the cannula may be inserted. The cannula defines a pathway through a body wall through which the surgical instruments are placed. Finally the seal valve and seal housing provides an isolation of the cannula so that if insufflation is employed the body region remains distended and sealed. All three components are usually fitted together and used as a single unit for passage by one or more surgical instruments through the body wall and into a body cavity.

Laparoscopic surgery typically begins as the surgeon inserts a large bore needle through a body wall and into the internal region associated with the body wall. Next, an inflation or insufflation gas is pumped into the internal region until it is properly distended. The body wall and body cavity are now ready for insertion of trocars.

Typically, a small incision is made in the skin at a desired trocar location in the patient. The incision may be made via a scalpel or other sharp instrument. The trocar assembly, with the trocar extending out of the port, is then forced through the incision via the obturator which cuts or pierces the body wall, thereby widening the incision and permitting the port to extend through the incision, past any fascia, and into the body cavity. The obturator is then withdrawn, leaving the port in place.

If not already distended, an insufflation element may be attached to the trocar port in order to insufflate the surgical site. An optical element may then be introduced through the trocar port. Additional incisions and trocars and ports are then typically used so that additional laparoscopic instruments may be introduced into the body.

Trocar assemblies are manufactured in different sizes. Typical trocar port sizes include diameters of about 5 mm, 10 mm, and 12 mm, which are sized to permit variously sized laparoscopic instruments to be introduced therethrough including, e.g., graspers, dissectors, staplers, scissors, suction/irrigators, clamps, forceps, biopsy forceps, etc. While 5 mm diameter trocar ports are relatively small, in some circumstances where internal working space is limited (e.g., children), it is difficult to place multiple 5 mm diameter ports in the limited area. In addition, 5 mm diameter trocar ports tend to limit movement of instruments inside the body cavity to a great extent. Such a conventional 5 mm diameter trocar has a sealing valve and sealing mechanism and therefore the opening for the surgical instrument is limited.

Further, while laparoscopic surgery has reduced the trauma associated with various surgical procedures and has concomitantly reduced recovery time from these surgeries, there always remains a desire in the art to further reduce the trauma to the patient.

One area of trauma associated with laparoscopic surgery identified by the inventor hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen and inserting the optical device, two incisions for trocar ports for inserting graspers therethrough, and a fourth port for passing a stapler therethrough. Those skilled in the art and those who have undergone surgical procedures understand that even the 5 mm diameter trocar ports leave holes which must be stitched and which result in scars. Scar tissue may affect the internal portion of the fascia as well as the cosmetic appearance of the skin, which may be detrimental for the patient or even a surgeon if that area of the skin is subject to a later incision or medical procedure.

A second area of trauma associated with laparoscopic surgery relates to trauma resulting from the manipulation (e.g., angling) of the trocar ports required in order to conduct the surgery due to inexact placement. The port may need to be angled so that the instrument, for instance, can be placed within the body cavity to cut tissue or an organ, grasp it, or other actions during surgery. Angling of the port can cause tearing at the incision periphery. Such tearing can lead to extensive scar tissue and in general an extension of the incision area. Again, conventional 5 mm diameter trocars including a valve and sealing mechanism are hard to angle in regard to the opening for the surgical instrument. Thus a need exists for a surgical access port that is not subject to tearing fascia at the point of incision into the patient.

A further problem with having multiple surgical instruments within a body cavity at the same time via multiple ports, especially where the surgical instrument includes a needle tip is inadvertent needle penetration in tissue and resulting scarring or even more serious complications during the surgery if other tissue is nicked or penetrated unintentionally. Indeed, placing a sharp instrument such as an inflation needle or trocar obturator through a body wall and into an associated internal region comes with considerable risk. The human abdomen, for example, is a tightly packed region that is filled with delicate structures and organs. There is no open space between the abdominal wall and those structures or organs until inflation gas is inserted and a pneumoperitoneum is established. Great care must be taken when placing inflation needles so as to avoid penetration of intestine, bowel or other structures. Even after insufflation is established, there is a risk of injury during placement of additional sharp instruments through the distended body wall.

Yet another problem is the blunt force used by a surgeon in inserting a conventional trocar with an obturator. The body wall is comprised of skin, muscle, fat and a thin membrane. The wall may be thick, muscular and tough or it may be lean and soft. As such, placement of a blunt or sharp obturator through the body wall requires great skill and knowledge of what lies within the internal region. The force required to insert a blunt or sharp obturator through a body wall can exceed forty pounds in some cases. This applied force easily overcomes the pneumoperitoneum and forces the body wall down and against delicate structures where there is the danger of piercing or cutting those structures. Further, the force needed to pierce the body wall may result in excessive tearing of the skin and scarring.

To combat the need for such force of insertion of a typical trocar, some surgeons have also used a technique referred to as a "cut down" procedure where successive small incisions are made until the body wall is cut through, at which time a blunt trocar or a trocar obturator is inserted with a certain level of force. This process may incur less force but it is time-consuming and may leave a deeper and larger scar.

Therefore a need exists for a surgical access port which is easier to insert into a body wall.

There continues to be a need in the art for a surgical access port which reduces trauma to the patient, reduces complications to the patient, does not lead to extension of the incision area, does not lead to increased scar tissue generation, is easy to make and use, and improves safety while reducing costs to health care providers and patients and reducing the surgical time for a procedure which in turn may reduce costs and complications. The inventive needlescopic surgical instrument including a surgical access port has a trocar having a cannula with a diameter of about 1 mm to about 3 mm which is inserted into a patient's skin and body wall via the needlescopic surgical instrument, meaning a surgical instrument which includes a needle tip on the lumen or cannula of the surgical instrument.

While conventional trocars, typically including an obturator, are known, the conventional art includes a cannula with a diameter exceeding about 5 mm. Thus there exists a need for a surgical access port which includes a smaller diameter cannula.

Further, the conventional trocars are inserted manually through force and thus a need exists where a surgical access port may be inserted via a needlescopic surgical instrument wherein the instrument has a needle for insertion into the patient's skin and body wall. These and other needs are met by the inventive surgical access port assembly and method for insertion and method of use.

Additionally, conventional trocars include a valve and sealing means so as to prevent gas leakage during insufflation. A need exists for a more streamlined surgical access port without an additional valve or sealing means while still maintaining sufficient insufflation during surgery. A need exists for a surgical access port without a sealing valve or sealing means while still maintaining an acceptable gas pressure level or minimal leakage. A further needs exists for a surgical access port which is less expensive than expensive conventional trocar assemblies and laparoscopic instruments.

Other advantages of the present invention will become apparent from the following description and appended claims.

SUMMARY OF THE INVENTION

It is therefore an object of the invention to provide a minimally invasive surgical assembly and method of use which reduces trauma to the patient relative to presently used assemblies, such as trocars and conventional surgical access ports.

In accord with the objects of the present invention, which are discussed above and will be discussed below, an exchanger surgical access port assembly according to the invention broadly includes a cannula having a diameter of less than about 3 mm and a tapered hub. The hub is capable of attachment to a laparoscopic surgical instrument and the hub is connected to the proximal end of the cannula. The inventive surgical access port assembly does not include a sealing valve or a sealing mechanism as found in conventional trocars.

BRIEF DESCRIPTION OF THE DRAWINGS

FIG. 6 is a top view of an embodiment of the surgical access port of the present invention connected to a needlescopic lumen.

FIG. 7 is an exploded view of an embodiment of the surgical access port assembly of the present invention connected to the needlescopic surgical instrument.

DETAILED DESCRIPTION OF THE INVENTION

Figure 1:
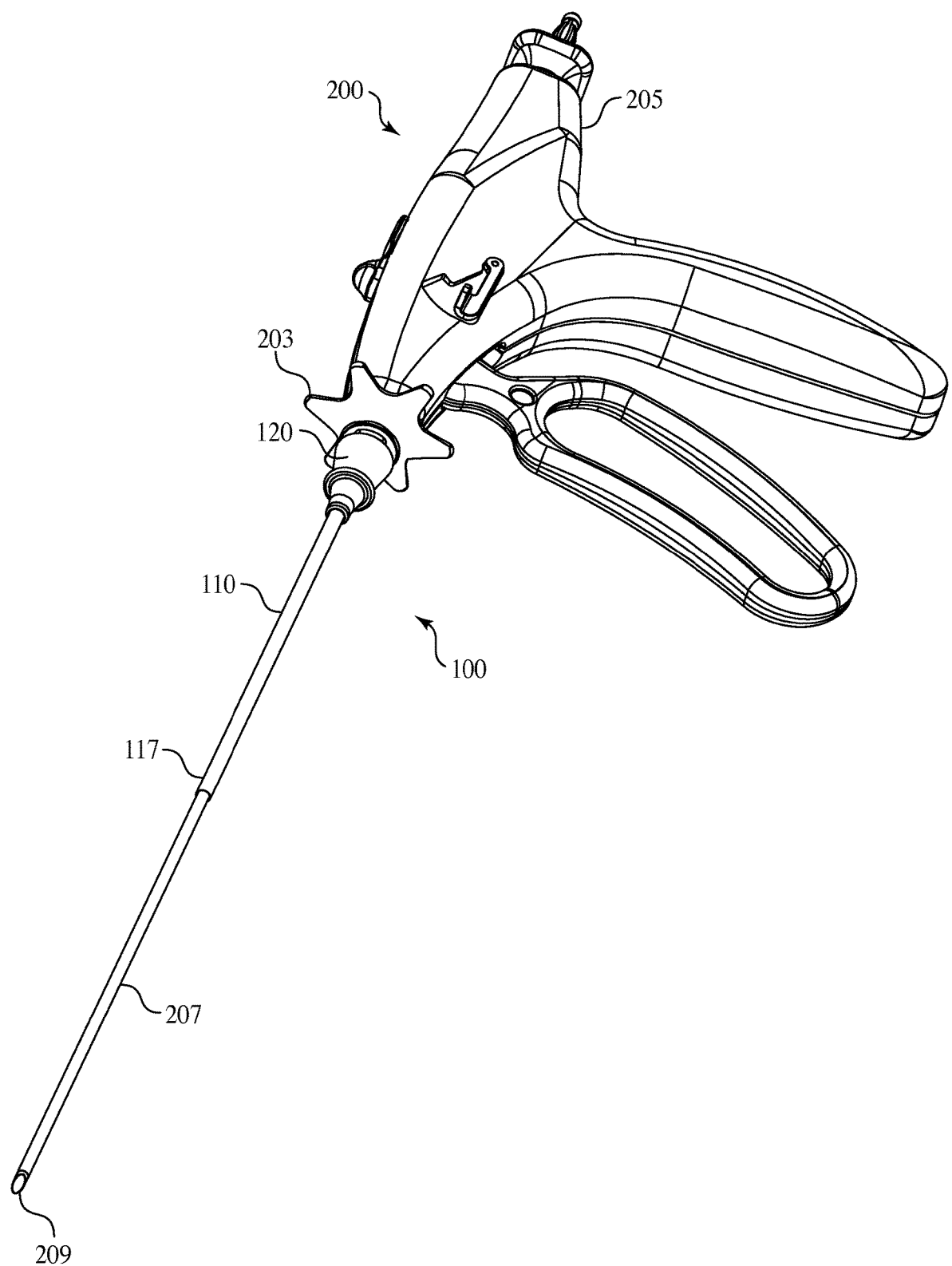
FIG. 1 is one embodiment of the surgical access port assembly of the present invention connected to the needlescopic surgical instrument.
Figure 2:
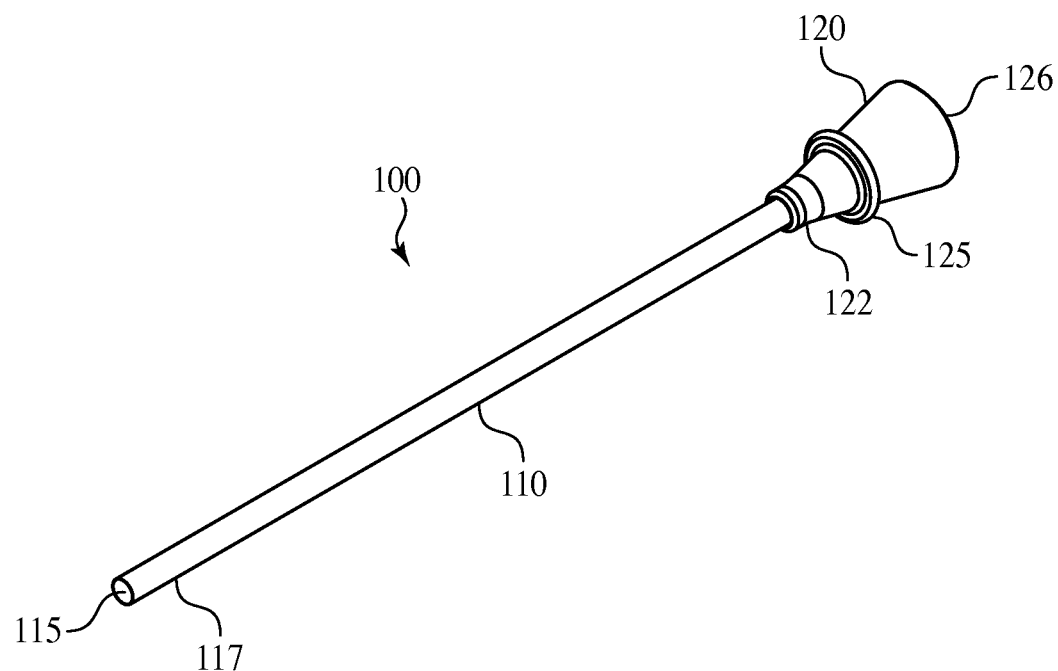
FIG. 2 is a perspective view of an embodiment of the surgical access port assembly of the present invention.

Reference will now be made to the drawings wherein like reference numerals identify similar structural features or aspects of the subject invention. For purposes of explanation and illustration, and not limitation, exemplary embodiments of a surgical access port assembly in accordance with the invention, or aspects thereof, are shown in FIGS. 1 through 8E. The surgical assembly of the invention is a low cost, easy to manufacture, surgical access port assembly, which can be used, for example, during minimally invasive surgical procedures to reduce trauma to a patient.

Examples of minimally invasive surgical assemblies and related equipment are described in U.S. Pat. No. 7,766,937 to Ravikumar, U.S. Pat. No. 8,230,863 to Ravikumar et al., U.S. Pat. No. 8,313,507 to Ravikumar, U.S. Pat. No. 8,133,255 to Ravikumar et al., U.S. patent application Ser. No. 11/685,522 to Ravikumar et al (published as U.S. Patent Pub. No. 2007/0250112), U.S. patent application Ser. No. 12/503,035 to Ravikumar (published as U.S. Patent Pub. No. 2010/0016884), U.S. patent application Ser. No. 12/689,352 to Ravikumar et al (published as U.S. Patent Pub. No. 2010/0292724), U.S. patent application Ser. No. 11/610,746 to Ravikumar et al. (published as U.S. Patent Pub. No. 2007/0282170), and U.S. patent application Ser. No. 12/689,352 to Ravikumar et al. (published as U.S. Patent Pub. No. 2010/0292724), all of which patents, applications, and publications are incorporated by reference herein in their entireties.

The present invention includes an exchanger surgical access port assembly 100, which includes a surgical access port including a cannula and a hub. The inventive surgical access port 100 is connected to a laparoscopic instrument having an elongated cannula, optionally including a needle (a needlescopic surgical instrument), such that the surgical access port is placed over cannula and thus does not require an obturator as the needle of the surgical instrument pierces the patient's skin and thereafter the surgical access port 100 is moved down the cannula and inserted into the incision at the surgical site.

The surgical access port assembly 100 includes a cannula 100 with a diameter of about 1 mm to about 5 mm (±20%) thereby reducing trauma to the patient and eliminates the need for a larger incision point or for a series of small incision cuts through the various layers of fascia. The diameter of the cannula 100 is preferably less than about 3 mm, preferably between about 2.0 mm to about 2.96 mm. The incision point may be about 4 mm or less depending on the diameter of the distal tip portion of the needle 209 of the laparoscopic surgical instrument 200. The inventive surgical access port assembly has a smaller diameter and thus a smaller incision point and working area within the body wall of the patient. Thus the potential scarring area is smaller and there is potential for reduced complications. Further, as the diameter of the cannula is smaller there is reduced tearing of the skin when the surgical access port assembly is angled during use in surgery when a surgical instrument is within the surgical access port. The smaller the diameter and surgical working area within the body wall (not the body cavity itself) the better during the surgery. The smaller diameter should not affect the working area within the body cavity during the surgery thus maintaining the effectiveness and efficacy of the surgical process. The smaller diameter of the cannula of the surgical access port assembly is particularly useful in pediatric patients, geriatric patients and other patients where the body wall may be negatively affected by a larger incision point and port access area.

Referring now to FIGS. 1 through 5, an embodiment of the present invention is shown of a surgical access port assembly 100. The surgical access port 100 has an elongated cannula 110. The distal end 117 of the elongated cannula 110 may be blunt or beveled. The elongated cannula 110 has a hollow shaft, a cannula shaft 115, through which surgical instruments may enter when the surgical access port is in use. The elongated cannula 110 has a proximal end connected to a hub 120. The hub 120 has a diameter, which expands outwardly from the proximal end of the elongated cannula 110. The hub 120 includes a portion 122 connected to the proximal end of the elongated cannula 110, an outer ring portion 125 which may be used for manual manipulation of the surgical access port 100, and an open end tapered portion 126 of the hub with a diameter exceeding that of the elongated cannula 110. The open end portion 126 of the hub 120 is capable of providing access for surgical instruments and devices during surgery. Further the open end portion 126 of the hub 120 may be connected to a portion of proximal end 203 of a surgical instrument cannula 207. The connection of the hub 120 of the inventive surgical access port 100 to the surgical instrument's hub 203 may be via friction, force, or snapped onto the hub 203.

The surgical access port 100 may be made of various materials such as rigid materials such as metals, for example stainless steel, as well as rigid plastics such as liquid crystal polymer or polycarbonate, glass-filled polycarbonate, or the like. The material should be compatible with the human fascia, body wall and any body cavity into which it is inserted so as to prevent or reduce any allergic reaction by the patient upon insertion. Optionally, the surgical access port 100 may be covered on the outside or even within the cannula shaft 117 with an insulating material (not shown) to prevent electrical current transfer to the patient, for instance upon inadvertent contact with an electrical surgical apparatus such as a monopolar or bipolar surgical instrument. The insulating material may be a plastic shrink wrap or any other insulating materials such as plastics, polymers, elastomers and the like, and combinations thereof.

Figure 3:
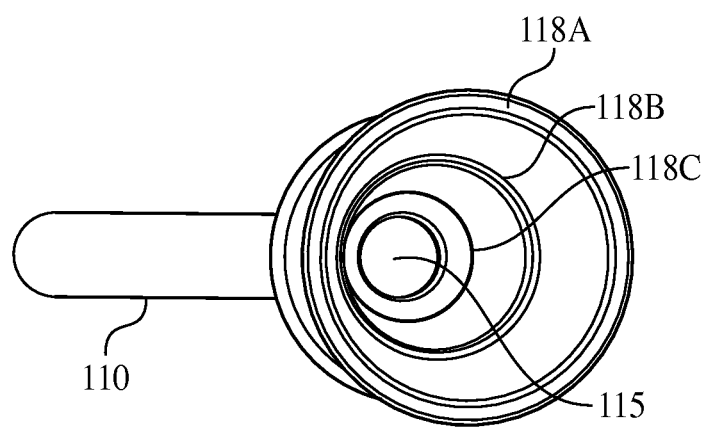
FIG. 3 is a view of an embodiment of the surgical access port assembly of the present invention looking inward from the hub.
Figure 4:
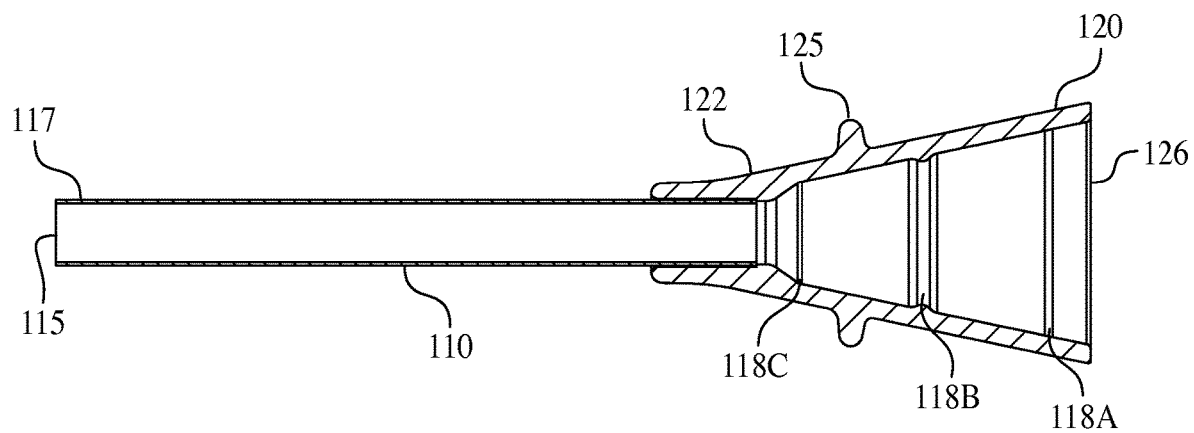
FIG. 4 is a side view of an embodiment of the surgical access port of the present invention.

Turning to FIGS. 2 through 5, the hub 120 of the surgical access port 100 has an inner portion including at least one inner ring 118, shown in FIGS. 3 and 4 as one embodiment of at least three inner rings 118A, 118B and 118C. Each of these inner rings 118 is a securing means for attachment of the surgical access port 100 to a surgical instrument 200 or other device over such instrument's cannula 207. Optionally, one of the inner rings 118 may be an O-ring made of a compressible material so as to seal a portion of the surgical access port 100 and deter the leakage of gas during surgical insufflation. For instance the O-ring may be made of rubbers, foams, plastics, silicones, fluorocarbons, polymers, elastomers, nitriles and the like, including combinations thereof.

Figure 5:
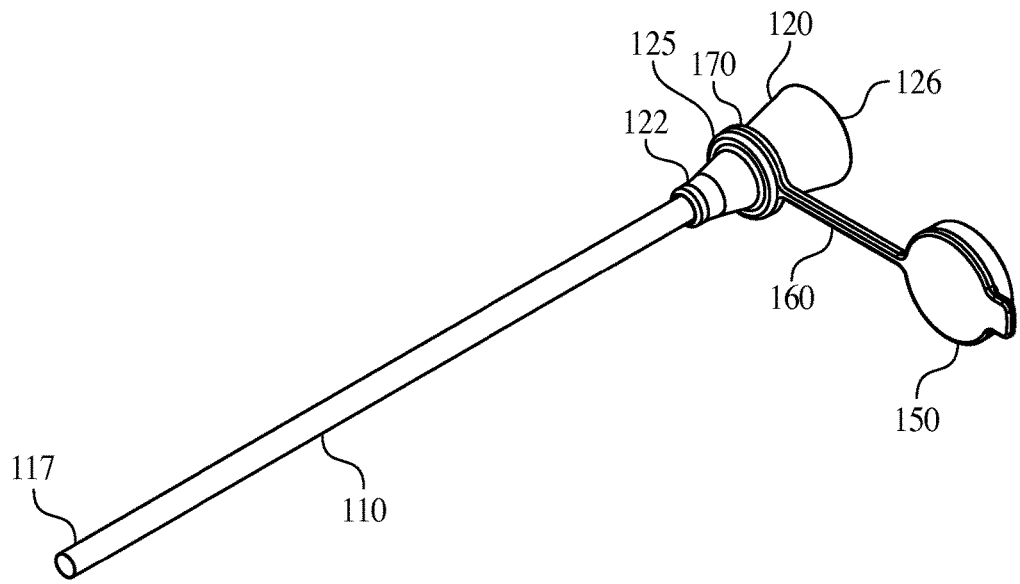
FIG. 5 is an embodiment of the surgical access port of the present invention including an optional cap.

The surgical access port 100 may also include a cap 150, as seen in FIG. 5, connected to the hub 120 via a cap tether 160 and a ring 170 on the hub 120. In use, once the surgical access port 100 is inserted into the patient's body, during surgery there may be a time when the original incision surgical instrument is not being employed in the patient's body and it is withdrawn such that the surgical access port 100 is not in use, therefore the cap 150 may be inserted into the open end portion 126 of the hub 120 and the opening sealed for anti-contamination reasons and also resulting in less gas leakage during surgical insufflation. For instance, when one surgical instrument is removed and before the next is exchanged or inserted the cap 150 may be employed. Thereafter at any time during the surgery when the exchanger surgical access port does not include any surgical instrument within the elongated cannula 110 the cap 150 may be used.

FIGS. 6 and 7 show another embodiment of the present invention wherein the surgical access port 100 is connected to a needle lumen 400 having a lumen shaft 420 and an end effector such as a needle 410, which needle lumen 400 may be inserted into a resposable handgrip surgical instrument or any other surgical instrument. The needle lumen 400 is inserted into an aperture of the surgical access port 100 via the open end tapered portion 126 of the hub 120 through to the shaft 117 of the elongated cannula 110. As seen in FIG. 7, the surgical access port 100 is thus connected to the needle lumen 400 in this embodiment by friction and light compression of the inner rings 118A, 118B and 118C of the hub 120 against a hub 430 of the needle lumen 400. Other connection or securing means may be used in other embodiments.

In use the needle of the needlescopic surgical instrument is used to penetrate the patient's fascia, the exchanger surgical access port assembly 100 is moved in an axial movement down the needle lumen via manual manipulation of the outer ring 125 and the surgical access port 100 is inserted into the patient's fascia and through the body wall. Generally, the surgical access port 100 is attached to the lumen of a percutaneous instrument, or single needle lumen, by pressure, friction or snapping on to the back of the exposed lumen. The surgical access port 100 is then advanced along the lumen, away from the percutaneous instrument, into the patient's fascia, through the body wall and into a body cavity when and as required and will remain in the body cavity as the lumen is removed and such initial instrument may be exchanged and replaced with a different instrument.

Further disclosed is a surgical instrument including a surgical access port 100. For instance, a needlescopic instrument having a lumen with a diameter of less than about 3 mm, preferably between about 2.3 mm to about 2.96 mm, with the lumen including a needle and optionally additional end-effectors such as jaws, dissectors, scissors, spatulas, cauterizers and the like including any known or later developed end-effectors. The exchanger surgical access port assembly 100 can be placed around the lumen that in normal working of the surgical instrument is outside of the patient, but can be unattached, and inserted into the patient's fascia, providing a guide for additional percutaneous instruments to be exchanged and inserted therein.

Figure 8A:
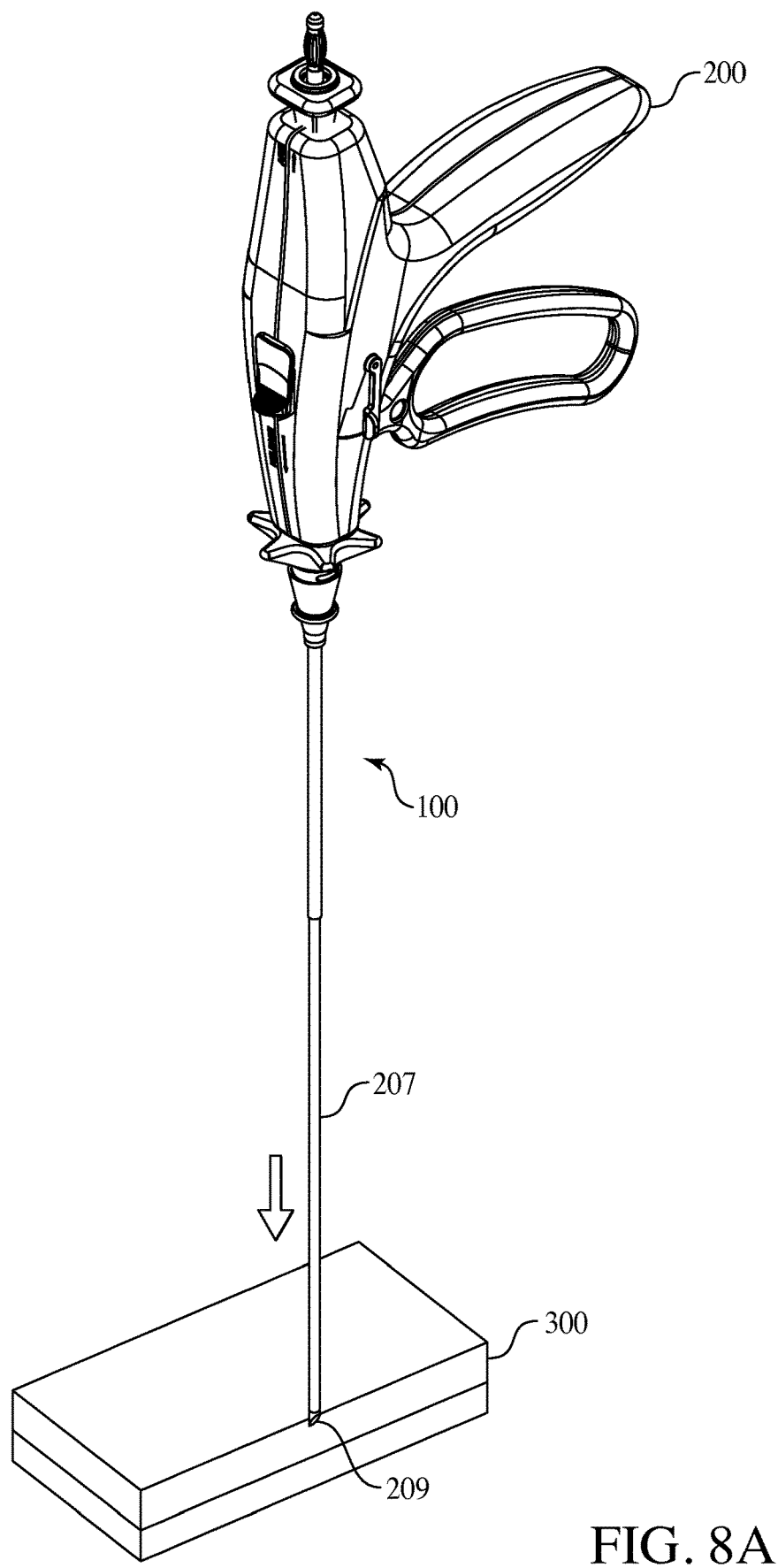
FIGS. 8A through 8E are an embodiment of a method of use of the present invention.
Figure 8B:
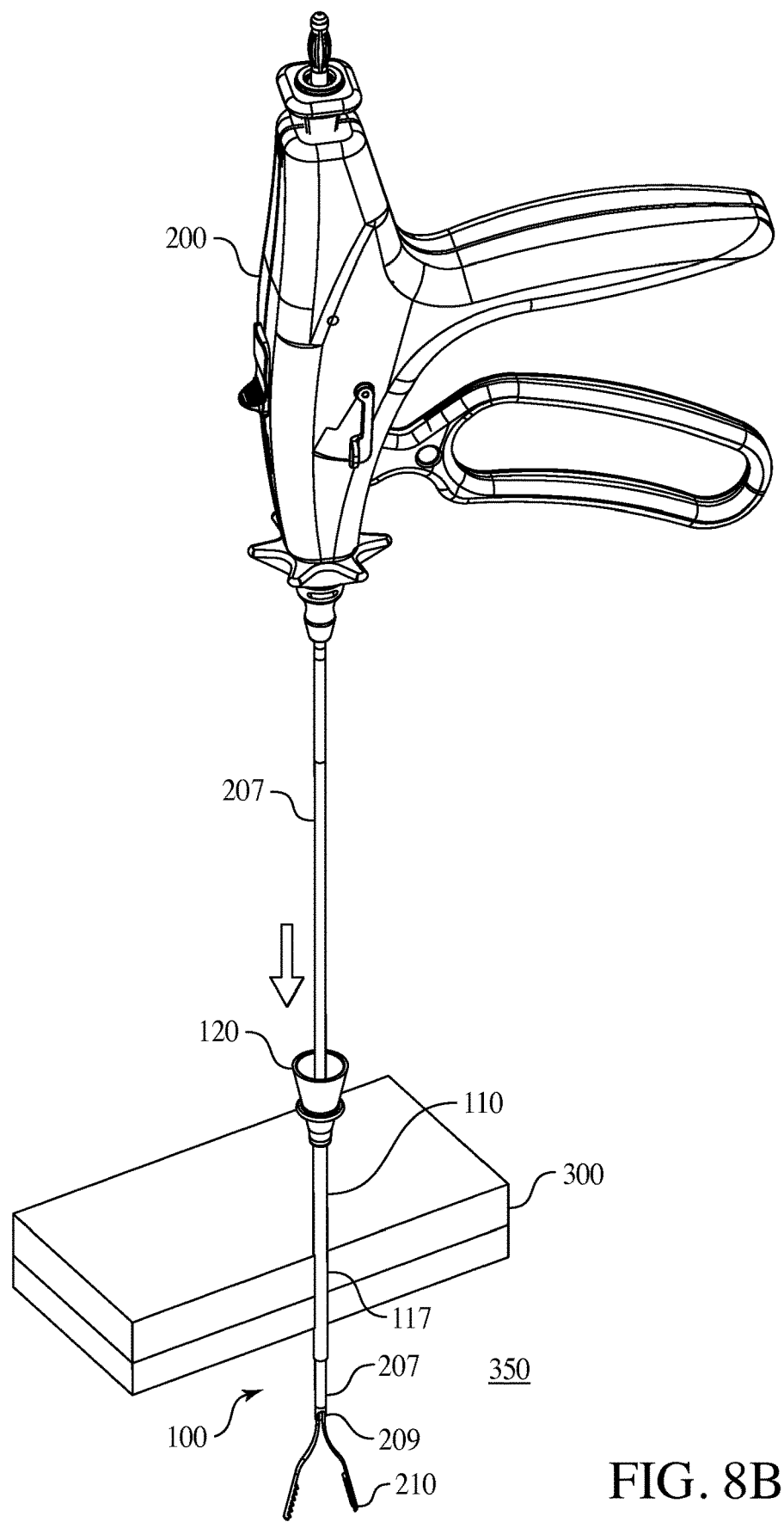
Figure 8C:
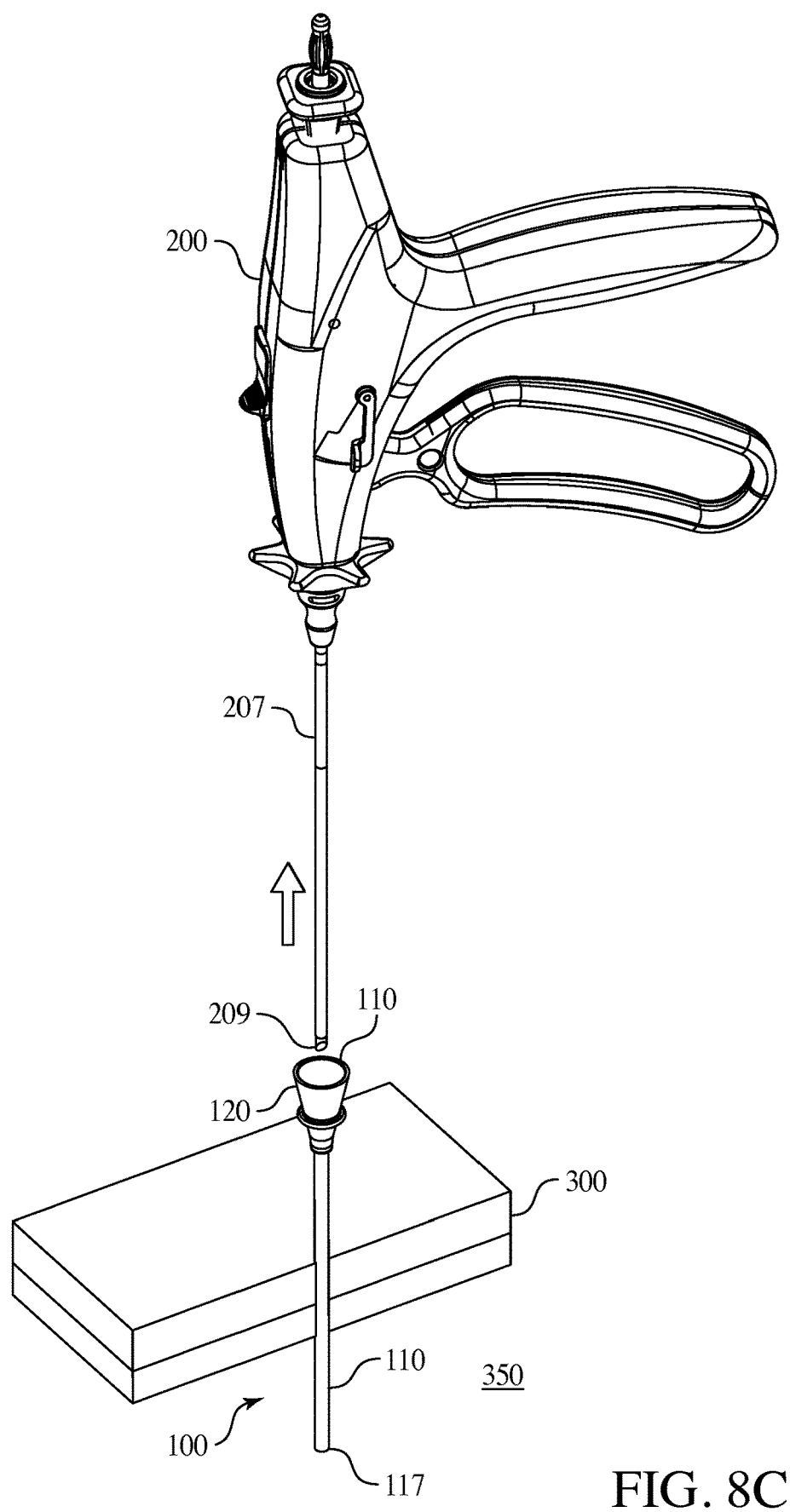
Figure 8D:
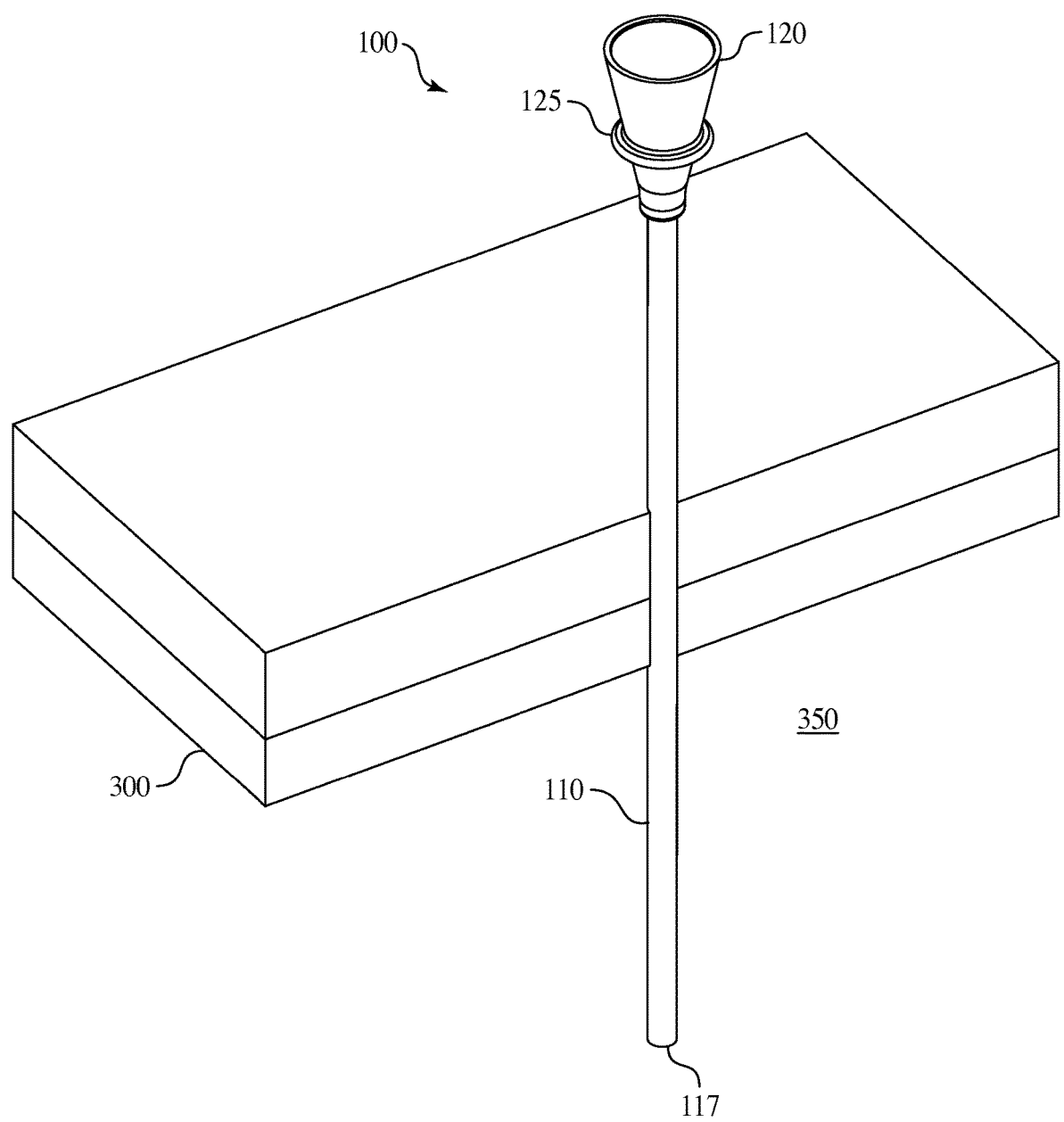
Figure 8E:
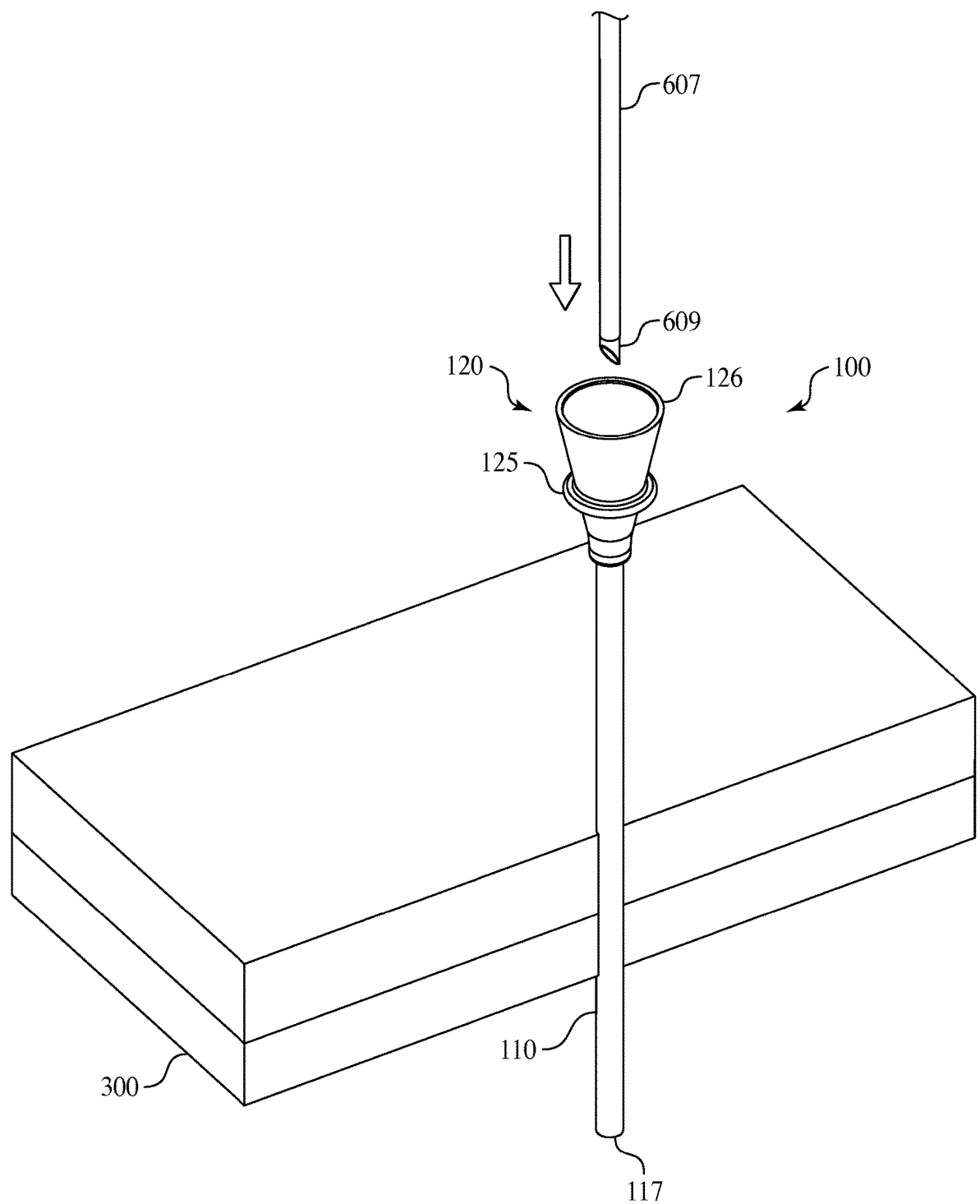

The following refers to FIGS. 8A through 8E and describe one method in which the surgical access port 100 could be utilized when in surgery wherein the surgical access port 100 is connected to a surgical instrument. In such an embodiment the percutaneous surgical instrument 200 could be pre-packaged with surgical access port 100 connect in place or the surgical access port 100 could be separate and is placed onto percutaneous instrument 200 by the user prior to inserting the distal end of a lumen 207, or a needle 209, of the instrument into the patient's fascia, body wall 300 and body cavity 350 as seen in FIG. 8A. Next the percutaneous instrument shaft traverses the body wall 300 and the instrument working end is used as an operative instrument. At some time the surgeon withdraws the surgical instrument 200 as shown in FIG. 8C. Then the surgical access port 100 is used by the surgeon to insert a different instrument into the same position as the original instrument. As seen in FIG. 8B, the surgical access port 100 is advanced over the instrument shaft, or lumen, into the body wall 300 and into a body cavity 350. The surgeon may then employ the surgical instrument 200 and engaged the end effectors, in this embodiment shown as graspers 210. Thereafter as shown in FIG. 8C the original instrument is removed from the body and is independent from the surgical access port 100. At this point in the method the surgical access port 100 is left in the body cavity 350 as seen in FIG. 8D. The body cavity 350 is therefore accessible for various surgical instruments via the surgical access port 100. Optionally, if included, a cap 150 on the hub 120 of the surgical access port 100 may be inserted to seal the body cavity 350 opening accessible through the surgical access port 100. At a later time during the surgery a new instrument 600 (not shown) is exchanged and inserted into the surgical access port 100 as seen in FIG. 8E with the cannula 607 and the needle end 609 being set for insertion into the surgical access port 100 via the hub opening 126. A number of instruments may be exchanged and access the body cavity 350 via the surgical access port 100 throughout the surgery. In this embodiment the further surgical instrument is shown with a needle tip 609 but also could be any known end-effector such as a grasper, dissector, spatula, scissors and the like including any known or later developed end-effectors and in other embodiments the further surgical instrument could be a specimen retrieval bag and other known or later developed surgical instruments. Once the surgery is complete the surgical access port 100 may be removed manually, or may be slid back up the last instrument's shaft or lumen (i.e., 507), connected onto the back of said instrument's lumen, and removed from the patient's body cavity 350, back through the body wall 300 and out of the patient's fascia. Optionally, based on the smaller incision point in the body wall and smaller diameter of the cannula of the inventive surgical access port assembly, the surgeon may forgo the step of suturing the incision point once the surgical access port assembly is removed, resulting in a faster surgical time and reduced scarring to the patient's facia.

Further advantages of the surgical access port assembly 100 of the present invention include retention of abdominal pressure during an abdominal surgery. Also the inventive device when in use during a surgery may be self-sealing without compromising insufflation pressure. While not being bound by theory, it is opined that dynamic friction between the outer edge of the small diameter cannula 110 and the patient's fascia and body wall 300 result in minimal gas leakage during insufflation. Thus in use the surgical access assembly 100 of the present invention has a smaller diameter, smaller incision point, better angle for surgical instrument access into the body cavity, while still maintaining sufficient insufflation. The absence of a sealing valve and sealing mechanism results in lower friction, which in turn may improve precision during the surgery. Such improved precision also reduces the surgical time and duration of the surgery which in turn improves surgical recovery by the patient and may reduce surgical complications and scarring.

Unlike typical trocars, the inventive surgical access port 100 would be attached to the back end of the percutaneous instrument and would only be slid down the shaft of the instrument into the patient's body to provide re-access to the same site location if the percutaneous instrument were to be removed or exchanged. While trocars are independently inserted in to the body cavity, the surgical access port 100 differs as it is slid into the body cavity over an instrument pre-inserted into the body wall.

In one embodiment the surgical access port 100 and percutaneous surgical instrument could come packaged as a kit, whereby the surgical access port 100 is placed onto and snapped onto the lumen of the surgical instrument. It is also envisioned where the surgical access port 100 would be packaged separately, as a stand-alone product and is utilized whenever needed.

The following benefits, structure, and advantages are also contemplated by the present invention: improved surgical precision, reduced surgical time resulting in reduced trauma to the patient and possibly less scarring, reduced recovery time, less pain, easier angling, easier handling by the user of a surgical instrument inserted into the surgical access port assembly during surgery, and other benefits.

The methods and systems of the present invention, as described above and shown in the drawings, provide for minimally invasive surgical assemblies including exchanger surgical access port assemblies with superior properties including ease of assembly, use and operation. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A surgical access port configured to attach to a surgical instrument, the surgical access port comprising:
    a hollow cannula defining an interior shaft extending longitudinally therethrough and having a diameter of less than about 3 mm; and
    a tapered hub on a proximal end of the hollow cannula, the tapered hub having an inner conical surface with at least one inner ring on the inner conical surface, the at least one inner ring being configured to attach to the surgical instrument via friction or compression of the at least one inner ring.

2. The surgical access port of claim 1, wherein the hollow cannula has a blunt distal end.

3. The surgical access port of claim 1, wherein the hollow cannula has a sharp distal end.

4. The surgical access port of claim 1, wherein the at least one inner ring comprises three inner rings.

5. The surgical access port of claim 1, wherein the at least one inner ring comprises an O-ring.

6. The surgical access port of claim 1, further comprising a cap configured to seal the tapered hub.

7. A surgical assembly comprising:
    a surgical instrument having a distal needle tip, a lumen, and a handle assembly on a proximal end of the lumen; and
    the surgical access port of claim 1.

8. The surgical assembly of claim 7, wherein the hollow cannula has a blunt distal end.

9. The surgical assembly of claim 7, wherein the hollow cannula has a sharp distal end.

10. The surgical assembly of claim 7, wherein the at least one inner ring comprises three inner rings.

11. The surgical assembly of claim 7, wherein the at least one inner ring comprises an O-ring.

12. The surgical assembly of claim 7, further comprising a cap configured to connect to the surgical access port and seal the tapered hub.

13. A surgical method of using the surgical assembly of claim 7, the method comprising:
    inserting the hollow cannula of the surgical access port into a body wall while leaving the tapered hub outside the body wall;
    performing a surgical procedure with the surgical instrument; and
    withdrawing the surgical instrument from the surgical access port and from the body wall.

14. The surgical method of claim 13, further comprising inserting another surgical instrument through the surgical access port into body cavity of the body wall.

15. The surgical method of claim 13, further comprising inserting a cap into the tapered hub to seal the tapered hub.

16. The surgical method of claim 13, further comprising withdrawing the surgical access port from the body wall without suturing the body wall at the placement of the withdrawn surgical access port assembly.

17. The surgical access port of claim 1, wherein the surgical access port lacks a sealing valve and a sealing mechanism.

* * * * *